United States Patent [19]

McConnell et al.

[11] Patent Number: 4,969,746
[45] Date of Patent: Nov. 13, 1990

[54] COMPONENT INSPECTION APPARATUS AND METHOD

[75] Inventors: Bain C. McConnell; Clifford R. Marritt, both of Winston-Salem; John L. Nelson, Lewisville; Kenneth W. White, Lewisville, all of N.C.

[73] Assignee: R. J. Reynolds Tobacco Company, Winston-Salem, N.C.

[21] Appl. No.: 239,893

[22] Filed: Sep. 2, 1988

[51] Int. Cl.$^5$ .............................................. G01B 11/24
[52] U.S. Cl. ................................... 356/376; 356/394; 356/237; 358/106; 209/577; 209/586
[58] Field of Search ............... 356/372, 376, 394, 237; 358/101, 106; 209/576, 586, 577

[56] References Cited

U.S. PATENT DOCUMENTS

4,496,056  1/1985  Schoenig, Jr. et al. ............. 356/237

Primary Examiner—F. L. Evans
Attorney, Agent, or Firm—Grover M. Myers

[57] ABSTRACT

The apparatus of the invention comprises a lighting device for illuminating a component to be inspected to form a halo of light around a periphery of the component and a system for comparing the shape of the halo of light to a known acceptable shape. A camera may be used to detect the halo and a programmed computer may be used to perform image analysis of the shape of the halo to determine if it conforms to an acceptable shape.

25 Claims, 6 Drawing Sheets

COMPONENT INSPECTION APPARATUS AND METHOD

BACKGROUND OF THE INVENTION

1. Field of the Invention

This invention relates to inspection devices and particularly to a device to inspect small cylindrical components for surface defects.

2. Discussion of Related Art

Superior quality control of manufactured goods requires inspection of each component of the goods. Such inspection can be carried out manually but preferably is carried out in an automated manner to facilitate the inspection process.

Recently, cigarettes having a short fuel element, e.g. carbon fuel element, have been developed, see U.S. Pat. No. 4,714,082, issued Dec. 22, 1987 to Banerjee et al. The fuel element must have a consistent shape in order to be properly assembled into the final product. Advantageously, the fuel element is relatively small, for example, about 10 mm in length and about 4.5 mm in diameter. Such an element is considered to be defective if there is any loss of material on the outside surface of the part that is more than 0.2 mm deep (measured radially) and which manifests itself on at least one end of the element.

It would thus be desirable to provide a process and apparatus to identify any such defect and otherwise for detecting defects which are present on at least one end of any small cylindrical element. It is to be noted that image analysis, per se, is not new and has been used to determine the quality of components. However, there is no known system for using known image analysis techniques for easily and effectively detecting defects in the surface of the end of an article. There is, therefore, a need for such an inspection apparatus.

SUMMARY OF THE INVENTION

One object of the present invention is to provide an inspection apparatus and method according to which defects in the outside surface of a small cylindrical part can be easily and reliably detected.

Another object of the present invention is to provide an inspection apparatus and method according to which automated inspection of small cylindrical parts can be quickly and easily carried out so as to adapt the apparatus and method for use in an assembly line environment.

A further object of the present invention is to provide an inspection apparatus and method according to which defects as small as 0.2 mm can be detected in a component having a diameter on the order of 4.5 mm.

In accordance with the above and other objects, however, the present invention is an inspection apparatus having a conveyor for separating and delivering small cylindrical components individually to a pickup station where the components are picked-up and transported to an inspection station in a manner such that the free ends of each component are available for inspection. At the inspection station, the free ends of the components are illuminated. Cameras detect the illumination and a computer automatically determines any variations in the surface of the free ends.

A fluted wheel may be provided as the pickup station. Each flute is in communication with a vacuum source so as to hold one component in place. Each flute has a length which is less then the overall length of the elements so as to permit the ends of the elements to be exposed.

The inspection station may include a plurality of fiber optic elements which illuminate the free ends of the elements to produce a halo of light outlining the elements. For purposes of the present invention, the term "halo" is used to indicate a differentiated zone surrounding a central object. Thus, a halo of light is an area of light around the edge or perimeter of interest, which may be round, square, or any other shape.

The computer may be programmed to determine a plurality of point coordinates around the halo of light, and to calculate radii to each point coordinate. The radii are then compared to a reference. The reference may be an average of the radii.

The computer may be programmed to classify a component as bad when a predetermined number of consecutive radii of the component are outside of a predetermined range compared to the reference.

Also in accordance with the present invention, the component to be inspected may have a first free end. The component is illuminated at the inspection station adjacent the first free end.

The component to be inspected may also have a second free end and the component may also be illuminated at the inspection station adjacent the second free end.

The invention also contemplates the use of a device for singulating components to be inspected and presenting the singulated components to the pick-up station one at a time.

At the inspection station, a camera may be aimed at each free end to detect the halo produced and the computer may be connected to receive an output of each camera.

The invention also includes the method of inspecting components to determine defects, comprising illuminating a component to be inspected to form a halo of light around a periphery of the component and comparing the shape of the halo of light to a known acceptable shape.

BRIEF DESCRIPTION OF THE DRAWINGS

The foregoing and other objects of the present invention will become more readily apparent as the invention is more clearly understood from the detailed description to follow, reference being had to the accompanying drawings in which like reference numerals represent like parts throughout, and in which.

DETAILED DESCRIPTION OF THE PREFERRED EMBODIMENTS

Figure 1:
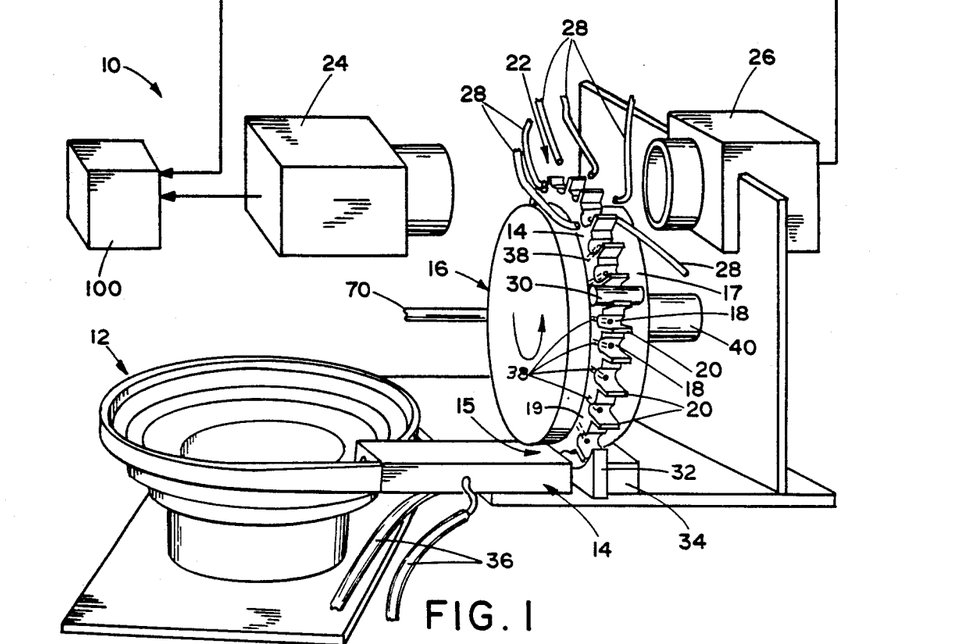
FIG. 1 is perspective view of the inspection apparatus according to the present invention.

FIG. 1 shows a perspective view of the inspection apparatus 10 of the present invention. Apparatus 10 includes a conventional commercially available helical vibratory bowl 12 which receives a plurality of the small components to be inspected for defects. In the preferred embodiment, the components have a cylindrical outer surface, it being understood that the invention is intended to be used with any components regardless of the shape of their outer surface.

Figure 2:
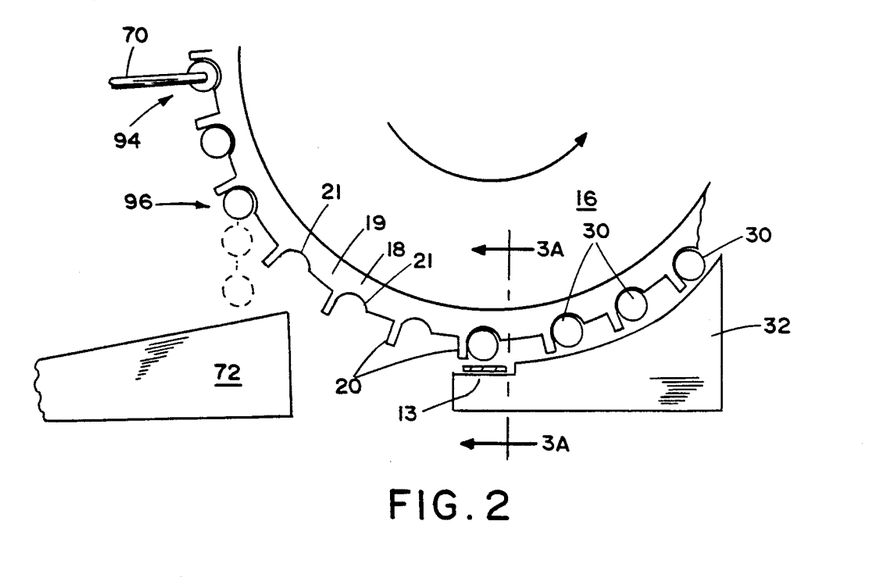
FIG. 2 is a part fragmentary view showing the pickup station of the inspection apparatus shown in FIG. 1.
Figure 3A:
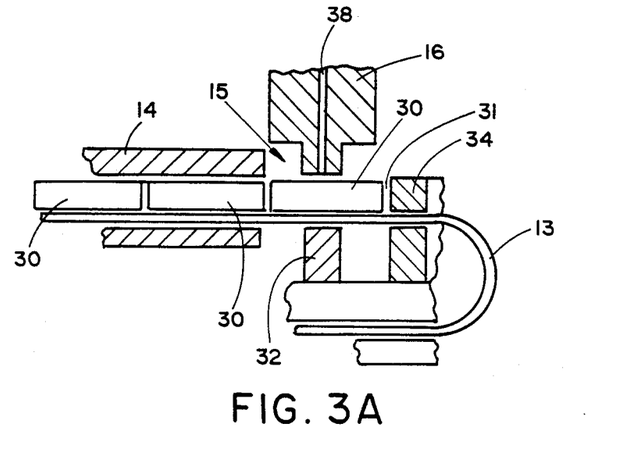
FIG. 3A is a sectional view of the inspection apparatus taken along line 3A—3A of FIG.
Figure 3B:
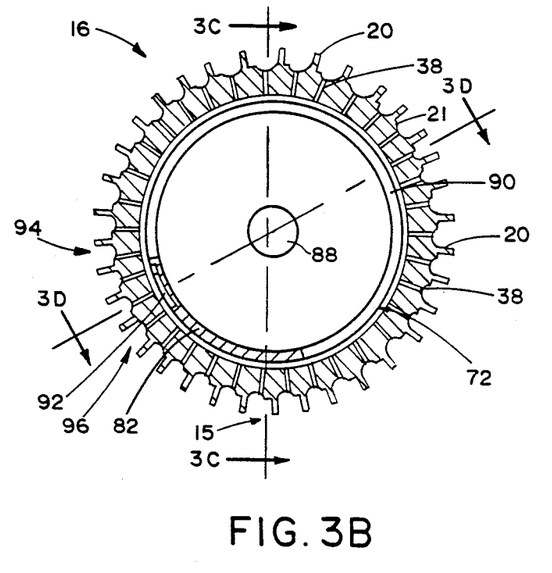
FIG. 3B is an elevational section view of the apparatus of FIG. 1.

The components are singulated by vibratory bowl 12 and moved into a transfer chute 14 where they are placed on a conveyor belt 13 (FIGS. 2 and 3A). The conveyor belt 13 presents the components one at a time to a pickup station 15. The cylindrical elements are picked-up by a fluted drum 16.

Drum 16 is manufactured for the inspection apparatus 10 and may be produced from any suitable material. In practice, drum 16 was machined from metal so as to have a large central section 17. A plurality of flutes 18 are formed in an axially narrow rib 19. The flutes 18 are seen more clearly in FIG. 2. Each flute includes a finger 20 which extends radially away from rib 19 and a recess 21 which is indented into the rib 19. Each recess 21 and rib 20 form a surface having a radius of curvature which is approximately the same as that of the outer surface of a rod-shaped fuel element 30 so that a fuel element 30 can be easily received by a flute. Also, as seen in FIG. 1, the rib 19 is narrower than the elements 30 so that each element 30 extends beyond both sides of the rib 19.

Drum 16 rotates in a counterclockwise direction as shown in FIGS. 1 and 2 so as to lift each fuel element 30 from the pickup station 15, which is tangential to the lowest point on the drum, to an inspection station 22 which is at the highest point on the drum. Inspection station 22 includes a front camera 24 for inspecting the front ends of the cylindrical elements and a rear camera 26 for inspecting the rear ends of the cylindrical elements. The ends of the elements are illuminated by a plurality of fiber optic elements 28. Six such fiber optic elements are shown in FIG. 1. Four of the fiber optic elements are bent upward at their ends to illuminate the underside of the fuel elements 30 and two fiber optic elements face down to illuminate the fuel elements from the top.

FIGS. 2 and 3A show the pickup station 15 in greater detail. As seen in FIG. 3A, the rod-shaped elements 30 are passed through a central aperture in transfer chute 14 in a queue, and forced out of the end of the transfer chute 14 against stop element 34. As seen in FIG. 2, a concave ramp or guide 32 has an upper curved surface which is spaced slightly from the free ends of fingers 20 so that as each fuel element 30 is moved off the belt 13 by a finger 20. Each fuel element 30 is maintained in close proximity to a recess 21 to facilitate pick-up by vacuum present in a channel 38. The stop member 34 is provided to stop the progress of the fuel elements 30 at the appropriate position on belt 13 to be picked up by the next flute.

The belt 13 is inside of the transfer chute 14 as shown in FIGS. 2 and 3A. The belt width is slightly larger than the diameter of the fuel elements. The belt 13 is driven at a speed which is slightly faster than the fuel elements are picked up to maintain an end-to-end queue of elements 30. As one element is swept out of the pick-up position 15 by a finger 20, another immediately takes its place ready to be picked up by the next finger 20. A pair of detectors 36 are provided on the chute 14 to detect the presence of the queue.

Referring again to FIG. 3A, it will be seen that at least one vacuum channel 38 communicates with the recess 21 of each flute. A conventional vacuum source (not shown) is in communication with the vacuum channels through a central channel formed in a shaft 40 which is part of a stationary drum 72 (FIGS. 3B-3E). A plurality of channels 38 are shown in phantom by dotted lines in FIG. 1.

FIGS. 3B-3E show the vacuum channels, the inner construction of the fluted drum 16 and the construction of stationary drum 72 in detail. Fluted drum 16 is actually mounted concentrically about stationary drum 72 for rotation on the shaft 40 of the stationary drum 72. As seen most clearly in FIGS. 3C and 3D, the fluted drum 16 has a cylindrical shaft 74 which is journalled on shaft 40. Shaft 74 may be driven through a motor and drive belt arrangement. Belt 76 of such a drive is shown.

Stationary drum 72 has an outer flange 78 and an inner wall 80 which are connected by a cylindrical wall 82. A circular plate 84 is attached to the flange 78 so as to form an enclosed interior space 87 of the drum 72. A central channel 88 in shaft 40 communicates with the interior space 87.

A slot 90 is formed through about 270 degrees of the cylindrical wall 82 from a position coincident with or slightly past the pick-up point 15 to just past a reject position 94 and just prior to an accept position 96. Slot 90 extends entirely through the wall 82 so as to allow the interior space 87 to communicate with the outside. In addition, an indentation 92 is formed in in the wall 82 at the accept position 96 to act as a pressure relief, as will be discussed below. The indentation 92 is cut from the flange 78 to about the middle of wall 82 but does not extend through to the interior space 87.

The stationary drum 72 and fluted drum 16 are machined to be closely adjacent but spaced by a sufficient amount to enable free rotation of the fluted drum. The channels 38 and the slot 90 are positioned relative to one another such that each channel 38 is aligned with the slot 90 during the time that that channel 38 rotates past the slot 90.

Figure 3C:
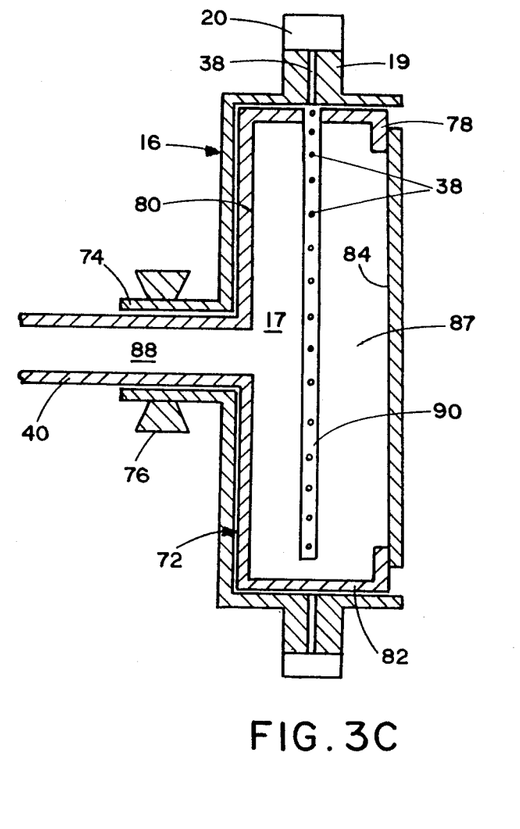
FIG. 3C is a sectional view of the apparatus taken along section line 3C—3C of FIG. 3B.
Figure 3D:
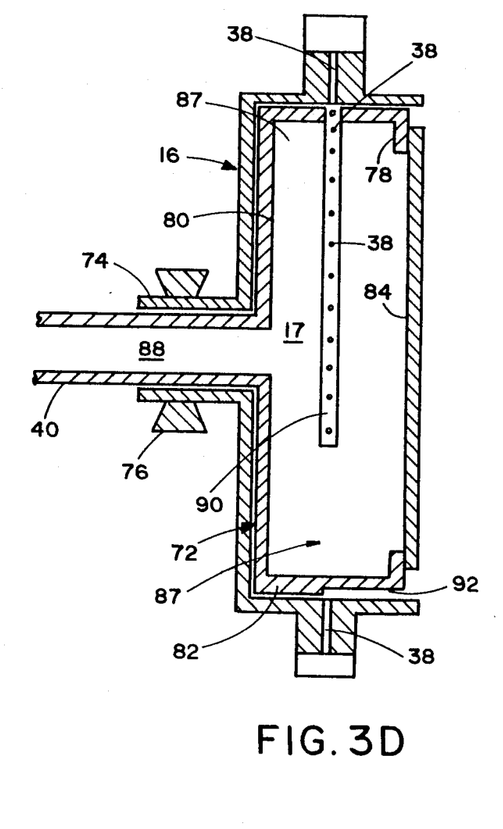
FIG. 3D is a sectional view of the apparatus taken along section line 3D—3D of FIG. 3B.
Figure 3E:
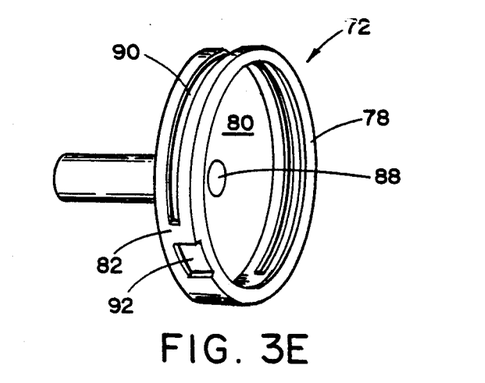
FIG. 3E is a perspective view of the stationary drum of the present invention.

Likewise, the channels 38 and the indentation 92 are positioned relative to one another such that each channel 38 opens above the indentation 92 as that channel rotates past the indentation. In this manner a pressure relief channel is formed from ambient to each channel 38 as the channel 38 rotates past the accept position, as shown at the bottom of FIG. 3D.

A vacuum is applied to the channel 88 so as to place the interior space 87 under vacuum. This vacuum is applied to each channel 38 as that channel rotates over the slot 90 as shown in the upper portion of FIG. 3C. When the channels 38 rotate over the portion of wall 82 in which no channel is formed, as shown in the lower portion of FIG. 3C, the vacuum is no longer applied. Finally, when the channels 38 rotate over the indentation 92, as shown in the lower portion of FIG. 3D, ambient pressure is applied to the channels 38 to release any vacuum still present.

In operation, as the fluted drum 16 rotates, vacuum is provided to each channel 38 to pick up an element 30 from the pick-up point 15. The element 30 is then rotated to the inspection station 22 by the rotation of drum 16.

It will be seen that the conveyor belt 13 provides a constant force to urge the elements 30 at the front of the queue out of transfer chute 14. The diameter of each element 30 is such that it can fit between the unrecessed portion of rib 19 and the upper surface of belt 13 to await the arrival of a flute. As each element 30 is moved into this position, its forward movement is halted by stop element 34 and it rests in position until a finger 20 contacts it, pushing it upward along the surface of ramp 32. At the same time, the vacuum is applied to channel 38 due to its alignment with the slot 90. The vacuum through channel 38 pulls the element 30 upwardly into a recess 21. Clearly, as each element 30 is swept away by a finger 20, the next element 30 moves into position on the upper surface of conveyor belt 13 ready to be picked up by the next finger 20.

Each element 30 is rotated past the inspection station 22 and then past the reject position 94. If that element is determined to be bad, as discussed below, it is removed at the reject position. Otherwise it proceeds on to the accept position 96. Just prior to the accept position, the slot 90 ends so that the vacuum holding element in position is removed, as shown at the bottom of FIG. 3C. At the accept position 96, the channel 38 holding the acceptable element moves over the indentation 92, as shown in the bottom of FIG. 3D. This allows ambient air pressure to reach the channel 38 through the pressure relief channel. The fuel element is then dropped onto a conveyor 72, as will be discussed further below.

As many channels 38 for each recess are provided as are necessary to pick up an element 30. The force of the vacuum through each channel also depends on the size, shape, weight, etc. of the elements 30. The combination of the number of channels 38 and the force of the vacuum provided is therefore chosen in dependence on the size, shape, weight and surface area of the elements to be picked up.

Figure 4:
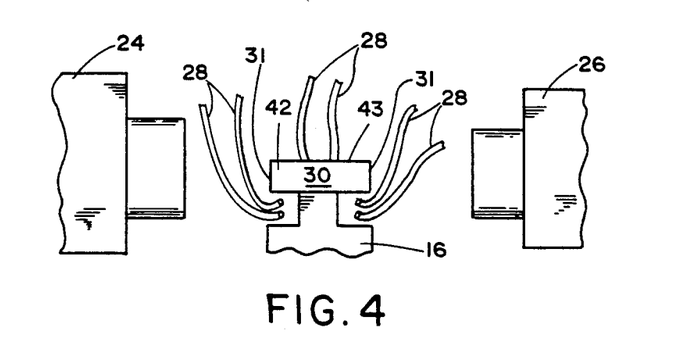
FIG. 4 is a more detailed view showing the inspection station of the inspection apparatus.

As the drum 16 is rotated by a motor (not shown) the elements are lifted to the inspection station 22 which is shown more clearly in FIG. 4. At the inspection station, the elements 30 are illuminated by the plurality of fiber optic elements 28 which are connected to individual light sources (not shown). The purpose of the fiber optic elements 28 is to illuminate the surface of each fiber optic element 30 towards it end portions 42, 43 without actually illuminating the surfaces 31 at the free ends. To this end, the rib 19 is narrower than the elements 30 so that the ends of the elements 30 can be illuminated from the top and from the bottom, as shown in FIG. 4.

The light pattern developed in this manner forms a halo which is detected by the cameras 24 and 26. For purposes of this invention, the term "halo" is used to mean a differential area of light around a central object. It is noted that, even though the elements shown have a cylindrical circumference, the invention can be used with other shaped objects, in which case the halo would conform to the shape of the outside of the object.

The outputs for the cameras are signals representing the detected light pattern. These outputs are transmitted to a computer 100 for analysis as will be discussed hereinbelow. The number and positioning of the fiber optic elements 28 depends on the size and shape of the element being inspected. Six fiber optic elements were found to work quite well with the type of carbon fuel element having the size and the shape discussed above (FIG. 1). Clearly, the fiber optic elements 28 must be positioned so as to illuminate the rod-shaped element without interfering with its travel. Preferably, the drum 16 continues to rotate without stopping at the inspection station and the fiber optic elements 28 are fixed in position so that the light from the fibers strikes the cylindrical surface but not the end surfaces of the rod-shaped elements.

Figure 5:
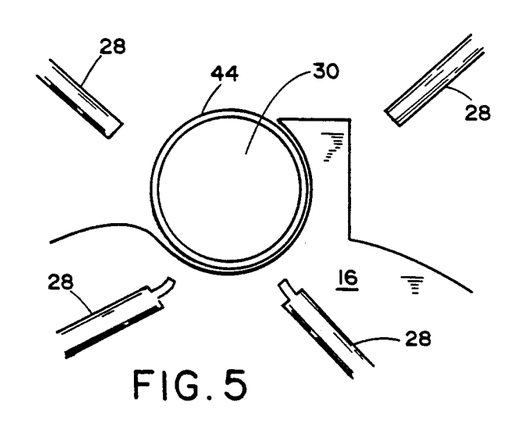
FIG. 5 is a view showing the halo produced by the optical fibers of the present invention.

FIG. 5 shows the optic fibers positioned to illuminate the bottom at one end of the element 30 as well as the optic fibers positioned to illuminate the top of the element 30. The two fibers illuminating the bottom on the other end of the element are not shown. In addition, FIG. 5 shows the result of the illumination. By illuminating the element 30 so that the ends 42 and 43 are not directly hit with light, a halo 44 of light is formed around the outer surface of the element 30 as viewed axially by the camera at that end of the element. This halo represents the shape of the surface of the element at that end of the element and will point out any defects. As shown in FIG. 5, the element is perfectly cylindrical and the halo is also cylindrical.

Figure 6:
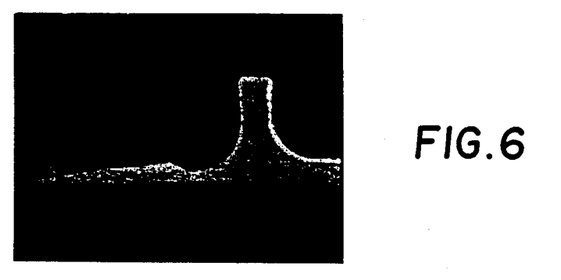
FIG. 6 is a copy of a photograph showing an illuminated flute without a cylindrical element.
Figure 7:
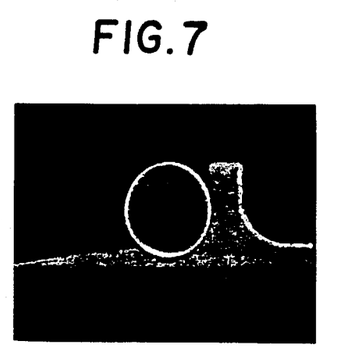
FIG. 7 is a copy of a photograph showing the actual halo produced on a good element.
Figure 8:
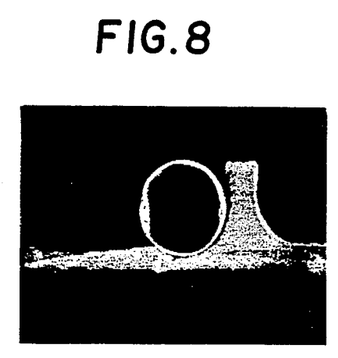
FIG. 8 is a copy of a photograph showing the actual halo produced on a bad element.

FIG. 6 shows the illumination of the flute which carries no rod shaped element. The sides of the flute and the non-recessed portion of the rib 19 next to each flute are illuminated slightly due to the placement of the fiber optic elements 28 which, as shown in FIG. 4, includes at least one element on each side of the flute. FIG. 7 shows the same flute with an acceptable rod shaped element. It will be seen that the halo in FIG. 7 is consistent about the circumference of the element. FIG. 8 shows a defective rod shaped element. On the left side of the figure it will be seen by the enlargement of the halo that a portion of the rod shaped element is missing.

Figure 9:
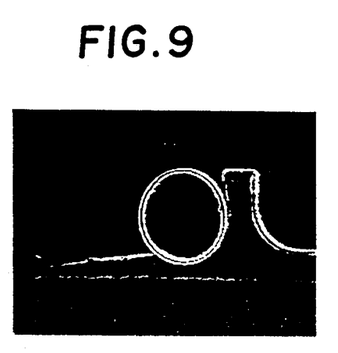
FIG. 9 is a copy of a photograph showing the halo as detected on a good element by Sobel processing which transforms a grey scale image into an image representing the rate of change in the image and thus can measure thickness of a defect.
Figure 10:
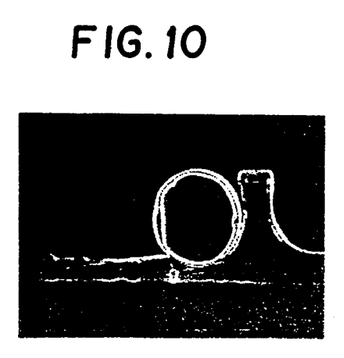
FIG. 10 is a copy of a photograph showing the halo as detected on a bad element by Sobel processing which transforms a grey scale image into an image representing the rate of change in the image and thus can measure thickness of the defect.

In FIGS. 6-10, all of the fiber optic elements are recessed behind the end face of the rib 19 so that the ends of the elements are not illuminated. FIGS. 9 and 10 show the halo after Sobel processing. As seen in FIG. 9 a double halo is produced due to the use of Sobel processing. Sobel processing is a well known digital image processing technique which transforms a gray scale image into an image representing the rate of change in the image. The image obtained by Sobel processing corresponds only to rapidly changing areas of light. FIG. 10 shows a defective element detected with Sobel processing. With this technique, the width of the defect can be readily calculated. The defect is shown in the inner halo which is truncated on the left hand side of the figure.

In order to determine if a rod shaped element should be accepted or rejected, conventional image processing techniques are used to identify the halo surrounding each element as it passes between cameras 24 and 26 of FIG. 1. As is well known to those skilled in the art, any images produced by light reflected from the flute or halos produced along the flute itself can be eliminated from the image to be computer analyzed. The halo of the cylindrical elements is analyzed using a program according to FIG. 11. In step 50, an attempt is made to determine the center of the halo. The center can be located by defining two diameters across the halo and calculating where the diameters cross. If the diameters cross at a point where four radii of unequal length are formed, it is determined that the center cannot be accurately located in step 52 and the part is rejected in step 54. If a center is located, control passes to step 56 where a large number of edge point coordinates are determined along the halo. For example, 256 edge point coordinates can be defined using known image processing techniques. The radii from the calculated center to each of the 256 edge point coordinates are then calculated in step 58. The average of these radii is then calculated in step 60. In step 62, the actual length of each radius is compared to the average to determine any deviation. A bad radius is defined as one having more than a certain percent deviation from the average. For example, in step 64, a bad radius is defined as having greater than a 7 percent deviation. The numbers of the radii which are bad are stored in step 64 and in step 66, a bad element is determined as having more than Y consecutive bad radii. Thus, in step 64, the depth of a defect is determined and in step 66, the circumferential extent of the defect is determined. If both the depth and the circumferential extent are greater than is considered acceptable, control passes to step 54 where the part is rejected. For example, if 5 consecutive radii deviate more than 7 percent from the average, the part may be considered defective and rejected in step 54. Otherwise, the part is kept and control passes to step 68.

Figure 11:
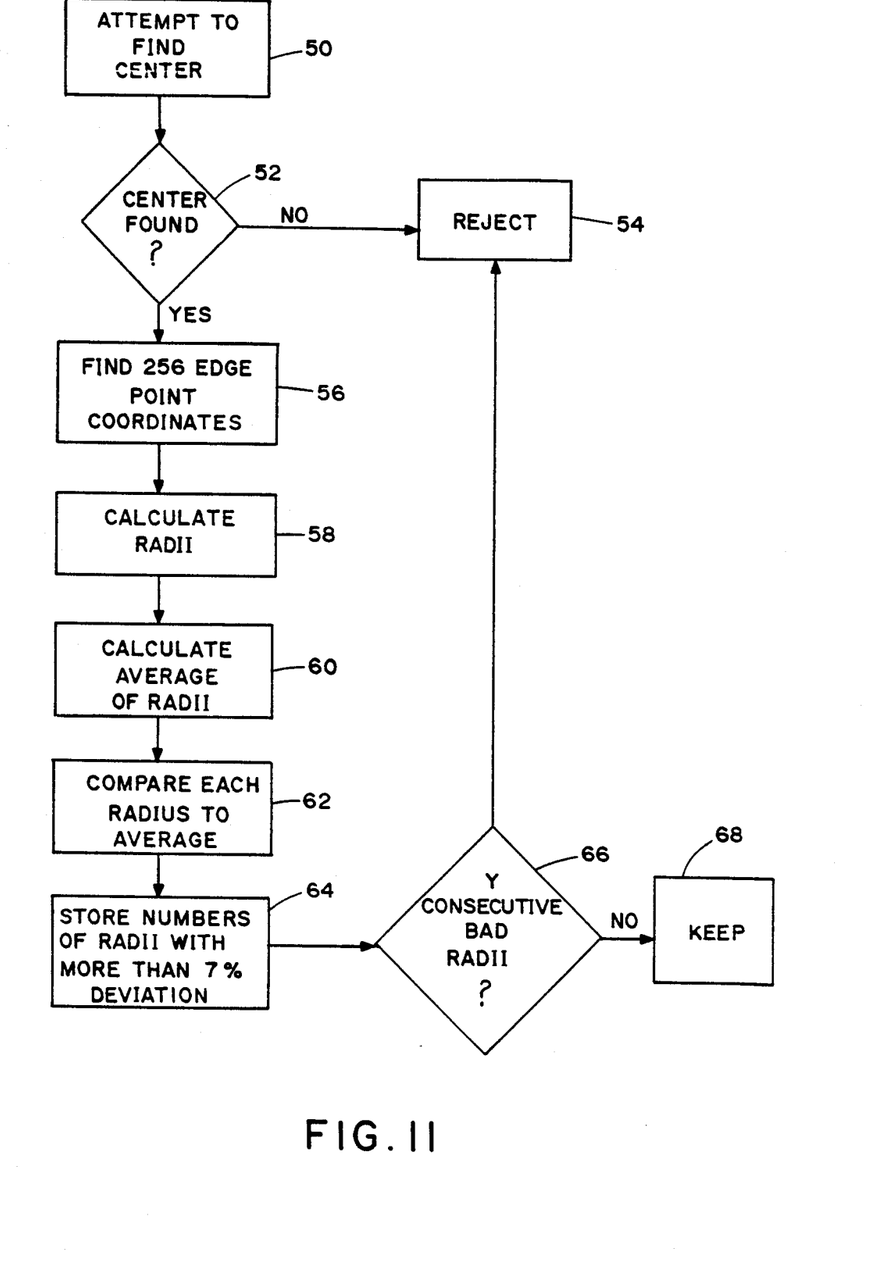
FIG. 11 is a flow chart showing the inspection software used in the present invention.

It will be understood that the 7 percent deviation in step 64 can consist of both radii which are too long and radii which are too short. Obviously, the program could be modified to determine only one or the other defect, if desired.

Referring again to FIGS. 1 and 2, a high pressure tube 70 can be placed at the reject position 94 of the drum 16 after the inspection station to remove rejected parts. When a rejected part is positioned in line with the high pressure tube 70, a high pressure shot of air is used to force the part backward into a reject bin.

If a part is acceptable, control passes to step 68 and the element is allowed to proceed to the accept position 96 where the vacuum is removed so that the part is dropped from the drum 16 onto the subsequent conveyor 72 as shown in FIG. 2. The structure for removing the vacuum at the accept position was discussed in detail above. Alternatively, a shot of pressurized air can be passed through the channel 38 in order to force the acceptable element from the fluted drum onto the waiting conveyor 72. This could be accomplished by communicating the indentation 92 with a high pressure source rather than ambient.

Conveyor 72 can lead to an accumulator to store the elements 30 until needed at a later processing station, or the operation of drum 16 can be synchronized with later stages so that the correct number of acceptable elements 30 is provided to the next processing station to be used immediately.

It is noted that the various controls for the vacuum source, the light sources, the cameras, etc. are well within the skill of the art and are not being discussed in detail here. The cameras and computer analysis system used can be, for example, a conventional vision system sold by Videk Corporation, a subsidiary of Eastman Technologies, Inc.

In accordance with the forgoing description, it will be seen that rod shaped elements can easily and accurately be moved from a first conveyor to an inspection station to be illuminated and characterized by a halo of light. The halo of light is then analyzed using computer techniques to determine whether the part should be accepted or rejected. The foregoing description is intended to set forth the preferred embodiments of the present invention. This description should not be considered to limit the invention, however. Numerous additions, substitutions and other changes can be made to the invention without departing from the scope thereof as set forth in the appended claims.

What is claimed is:

1. An apparatus comprising:
    means for illuminating a component to be inspected to form a halo of light around a periphery of the component; and
    means for comparing the shape of the halo of light to a known acceptable shape.

2. An apparatus according to claim 1 wherein said illuminating means is disposed in an inspection station and including means for transporting components from a pickup station to said inspection station.

3. An apparatus according to claim 2 wherein said transporting means comprises a fluted drum having flutes shaped to individually receive components.

4. An apparatus according to claim 3 including means for holding said components in said flutes by vacuum.

5. An apparatus according to claim 2 wherein said comparing means comprises means for determining a plurality of point coordinates around said halo of light, means for calculating radii to each of said point coordinates, and means for comparing each of said radii to a reference.

6. An apparatus according to claim 5 wherein said reference comprises an average of said radii.

7. An apparatus according to claim 5 including means for classifying a component as bad when a predetermined number of consecutive radii of the component are outside of a predetermined range of said reference.

8. An apparatus according to claim 1 wherein said component to be inspected has a first free end and said illuminating means illuminates said component adjacent said first free end.

9. An apparatus according to claim 8 wherein the component to be inspected has a second free end and said illuminating means illuminates the component adjacent said second free end.

10. An apparatus according to claim 2 including means for singulating components to be inspected and presenting said singulated components to said pick-up station one at a time.

11. An apparatus according to claim 8 wherein said illuminating means comprises fiber optic elements.

12. An apparatus according to claim 8 wherein said comparing means comprises a camera aimed at said free end and a computer connected to receive an output of said camera.

13. An apparatus according to claim 9 wherein said comparing means comprises a camera aimed at each free end of said component and a computer connected to receive an output of each camera.

14. An apparatus comprising:

means for presenting a plurality of rod shaped elements to an inspection station one at a time;

means for determining a shape of a periphery of said elements relative to a known shape, said determining means comprising means for producing a halo of radiation representing said shape of said periphery; and means for accepting or rejecting said elements based on said determined shape.

15. An apparatus according to claim 14 wherein said determining means further comprises means for transforming said halo of radiation into electrical signals.

16. An apparatus according to claim 14 wherein said means for producing a halo of radiation comprises a plurality of fiber optic elements directing light onto said elements at a position spaced from ends of said elements such that said ends of said elements are not illuminated.

17. A method, comprising:

illuminating a component to be inspected to form a halo of light around a periphery of the component; and comparing the shape of the halo of light to a known acceptable shape.

18. A method according to claim 17 wherein said illuminating step is carried out in an inspection station and including transporting components to be inspected from a pickup station to said inspection station.

19. A method according to claim 18 wherein said transporting step comprises carrying said components in a fluted drum having flutes shaped to individually receive components to be inspected.

20. A method according to claim 19 holding said components in said flutes by vacuum.

21. A method according to claim 18 wherein said comparing step comprises determining a plurality of point coordinates around said halo of light, calculating radii to each of said point coordinates, and comparing each of said radii to a reference.

22. A method according to claim 21 including classifying a component as bad when a predetermined number of consecutive radii of the component are outside of a predetermined range of said reference.

23. A method according to claim 17 wherein said component to be inspected has a first free end and said illuminating step comprises illuminating said component adjacent said first free end.

24. A method according to claim 23 wherein the component to be inspected has a second free end and said illuminating step comprises illuminating the component adjacent said second free end.

25. An apparatus according to claim 18 including singulating components to be inspected and presenting said singulated components to said pick-up station one at a time.

* * * * *